(12) United States Patent
Straub

(10) Patent No.: US 8,053,572 B2
(45) Date of Patent: Nov. 8, 2011

(54) ALKYL-ANALIDE PRODUCING METHOD

(75) Inventor: Alexander Straub, Wuppertal (DE)

(73) Assignee: Bayer CropScience AG, Monheim (DE)

( * ) Notice: Subject to any disclaimer, the term of this patent is extended or adjusted under 35 U.S.C. 154(b) by 691 days.

(21) Appl. No.: 11/817,373

(22) PCT Filed: Mar. 1, 2006

(86) PCT No.: PCT/EP2006/001871
§ 371 (c)(1),
(2), (4) Date: Aug. 28, 2008

(87) PCT Pub. No.: WO2006/092291
PCT Pub. Date: Sep. 8, 2006

(65) Prior Publication Data
US 2009/0209769 A1    Aug. 20, 2009

(30) Foreign Application Priority Data
Mar. 2, 2005    (DE) .......................... 10 2005 009 457

(51) Int. Cl.
*C07D 265/02* (2006.01)
*C07D 231/00* (2006.01)
(52) U.S. Cl. ...................................... 544/63; 548/374.1
(58) Field of Classification Search .................... 544/63; 548/374.1
See application file for complete search history.

(56) References Cited

U.S. PATENT DOCUMENTS

| | | | |
|---|---|---|---|
| 5,223,526 A | 6/1993 | McLoughlin et al. | |
| 5,416,103 A | 5/1995 | Eicken et al. | |
| 5,438,070 A | 8/1995 | Eicken et al. | |
| 5,914,344 A | 6/1999 | Yoshikawa et al. | |
| 7,674,807 B2 | 3/2010 | Wada et al. | |
| 7,745,483 B2 | 6/2010 | Dunkel et al. | |
| 7,842,710 B2 | 11/2010 | Dunkel et al. | |
| 2004/0204470 A1 | 10/2004 | Elbe et al. | |
| 2007/0060579 A1 | 3/2007 | Wachendorff-Neumann et al. | |
| 2007/0066673 A1 | 3/2007 | Dunkel et al. | |
| 2007/0082877 A1 | 4/2007 | Dunkel et al. | |
| 2007/0203148 A1 | 8/2007 | Dunkel et al. | |
| 2008/0293566 A1 | 11/2008 | Suty-Heinze et al. | |
| 2009/0286681 A1 | 11/2009 | Dahmen et al. | |
| 2010/0056786 A1 | 3/2010 | Straub | |
| 2010/0130743 A1 | 5/2010 | Wada et al. | |
| 2011/0009267 A1 | 1/2011 | Suty-Heinze | |

FOREIGN PATENT DOCUMENTS

| | | |
|---|---|---|
| CA | 2 556 081 A1 | 8/2005 |
| EP | 0 589 301 A1 | 3/1994 |
| EP | 0 589 313 A1 | 3/1994 |
| EP | 0 824 099 A1 | 2/1998 |
| WO | WO 93/11117 | 6/1993 |
| WO | WO 03/010149 A1 | 2/2003 |
| WO | WO 2004/103953 A1 | 12/2004 |
| WO | WO 2004/103975 A1 | 12/2004 |
| WO | WO 2005/075452 A1 | 8/2005 |

OTHER PUBLICATIONS

Rele, Shyam. Generation of Reactive Low-Valent Titanium Species Using Metal-Arenes as Efficient Organic Reductants for TiCl3: Applications to Organic Synthesis. J. Org. Chem. 2001, 66, 2990-2994.*
[Bogert, Marston. Researches on Quinazolines. XXXVIII. The Synthesis of Some New Analogs of Cinchophen and Intermediate Products. Chemical Laboratories of Columbia University Journal. 1927, 49, 2650-2654.].*
Bogert, M.T., and McColm, E.M., "Researches on Quinazolines. XXXVIII. Synthesis of some new analogs of cinchopen and intermediate products," *J. Am. Chem. Soc.* 49:2650-2654, American Chemical Society (1927).
Database CAPLUS on STN, Chemical abstracts, Accession No. 1998:699952, Hahn, H.-G., et al., "Anchimeric assistance in the rearrangement of dichloro-3-methyl-1,4-oxathianes to 2-chloromethyl dihydro-1,4-oxathiins," *Bull. Korean. Chem. Soc.* 19:1109-1112 (1998), abstract.
Database CAPLUS on STN, Chemical abstracts, Accession No. 1965:90918, Kovendi, A., and Kircz, M., "New synthesis for quinazoline N3-oxides and 1,2-dihydroquinazoline," *Chemische Berichte* 98:1049-1059 (1965), abstract.
Database File Registry on STN, Chemical abstracts, Accession No. RN 795292-48-7 (Dec. 2004), abstract.
Database File Registry on STN, Chemical abstracts, Accession No. RN 790679-71-9 (Nov. 2004), abstract.
Database File Registry on STN, Chemical abstracts, Accession No. RN 777875-56-6 (Nov. 2004), abstract.
Database File Registry on STN, Chemical abstracts, Accession No. RN 425399-14-0 (2002), abstract.
Database File Registry on STN, Chemical abstracts, Accession No. RN 194783-80-7 (1997), abstract.
Database File Registry on STN, Chemical abstracts, Accession No. RN 853689-32-4 (Jul. 2005), abstract.
Database File Registry on STN, Chemical abstracts, Accession No. RN 848249-78-5 (Apr. 2005), abstract.
Dixon, W.J., et al., "Kinetics and mechanism of the addition of water and ring-opening of 2-methyl- and 2-aryl-4*H*-3, 1-benzoxazines to 2-aminobenzyl esters in the acidic pH range; change in rate-limiting step with buffer concentration and evidence for a tetrahedral carbonyl addition intermediate," *J. Chem. Soc., Perkin Trans.* 2:1503-1509, Chemical Society (1997).
Hahn, H.-G., et al., "Synthesis of Trifluoromethylated Dihydro-1,4-Oxathiin-3-Carboxanilides Through Polymer-Bound Activated Ester," *Heterocycles* 48:2253-2261, Elsevier (1998).
Hari, Y., et al., "Efficient synthesis of *o*-alkynyl-*N*-pivaloylanilines from *o*-acyl-*N*-pivaloylanilines and lithium trimethylsilyldiazomethane," *Tetrahedron Lett.* 47:1137-1139, Elsevier Ltd. (Feb. 2006).
Tarzia, G., et al., "Synthesis and Structure-Activity Relationships of a Series of Pyrrole Cannabinoid Receptor Agonists," *Bioorg. Med. Chem.* 11:3965-3973, Elsevier Ltd. (2003).
International Search Report for International Application No. PCT/EP2006/001871, European Patent Office, Netherlands, mailed on Aug. 24, 2006.

* cited by examiner

*Primary Examiner* — Rebecca Anderson
*Assistant Examiner* — Samantha Shterengarts
(74) *Attorney, Agent, or Firm* — Sterne, Kessler, Goldstein & Fox P.L.L.C.

(57) ABSTRACT

The present invention relates to a process for preparing known fungicidally effective alkylanilides from acid chlorides and aminoacetophenone via hydroxyalkyl-substituted carboxanilides, alkenylanilides and benzoxazine derivatives.

10 Claims, No Drawings

ALKYL-ANALIDE PRODUCING METHOD

This application is a 35 U.S.C. §371 National Stage filing of International Application No. PCT/EP2006/001871, filed Mar. 1, 2006, which claims the benefit of the filing date of German Patent Application No. 10 2005 009 457.0, filed Mar. 2, 2005. The entirety of each of these applications is incorporated by reference herein.

The present invention relates to a novel process for preparing known fungicidally effective alkylanilides from acid chlorides and aminoacetophenone via hydroxyalkyl-substituted carboxanilides, alkenylanilides and benzoxazine derivatives.

It is already known that alkylanilides are obtained by reacting the desired acid chloride with the corresponding alkylaniline derivative (cf. EP-A 0 824 099, WO 03/010149).

Furthermore, it is known that alkylanilides are obtained when the corresponding alkenyl- or alkinylanilides are hydrogenated, it being possible to obtain the alkenylanilides from acylanilides by reaction with a phosphoric acid compound in a Wittig-like reaction (cf. WO 03/010149).

Thus, the present invention provides a process for preparing alkylanilides of the formula (I)

in which
$R^1$ represents hydrogen or fluorine,
$R^2$ represents hydrogen, halogen, $C_1$-$C_4$-alkyl or $C_1$-$C_4$-haloalkyl having 1 to 9 fluorine, chlorine and/or bromine atoms,
A represents the radical of the formula (A1)

in which
$R^3$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl,
$R^4$ represents hydrogen, halogen, cyano, $C_1$-$C_4$-alkyl, $C_1$-$C_4$-alkoxy or $C_1$-$C_4$-alkylthio,
$R^5$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, or
A represents the radical of the formula (A2)

in which
$R^6$ and $R^7$ independently of one another represent hydrogen, halogen, $C_1$-$C_4$-alkyl or $C_1$-$C_4$-haloalkyl having 1 to 5 halogen atoms,
$R^8$ represents halogen, cyano or $C_1$-$C_4$-alkyl, or $C_1$-$C_4$-haloalkyl or $C_1$-$C_4$-haloalkoxy having in each case 1 to 5 halogen atoms,
or
A represents the radical of the formula (A3)

in which
$R^9$ and $R^{10}$ independently of one another represent hydrogen, halogen, $C_1$-$C_4$-alkyl or $C_1$-$C_4$-haloalkyl having 1 to 5 halogen atoms,
$R^{11}$ represents hydrogen, halogen, $C_1$-$C_4$-alkyl or $C_1$-$C_4$-haloalkyl having 1 to 5 halogen atoms,
or
A represents the radical of the formula (A4)

in which
$R^{12}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms,
or
A represents the radical of the formula (A5)

in which
$R^{13}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to halogen atoms,
$R^{14}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulphinyl or $C_1$-$C_4$-alkylsulphonyl, or A represents the radical of the formula (A6)

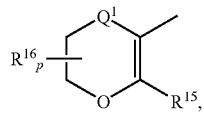

(A6)

in which
- $R^{15}$ represents $C_1$-$C_4$-alkyl or $C_1$-$C_4$-haloalkyl having 1 to 5 halogen atoms,
- $R^{16}$ represents $C_1$-$C_4$-alkyl,
- $Q^1$ represents S (sulphur), O (oxygen), SO, $SO_2$ or $CH_2$,
- p represents 0, 1 or 2, where $R^{16}$ represents identical or different radicals if p represents 2, or A represents the radical of the formula (A7)

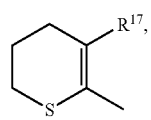

(A7)

in which
- $R^{17}$ represents $C_1$-$C_4$-alkyl or $C_1$-$C_4$-haloalkyl having 1 to 5 halogen atoms, or A represents the radical of the formula (A8)

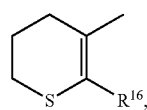

(A8)

in which
- $R^{18}$ represents $C_1$-$C_4$-alkyl or $C_1$-$C_4$-haloalkyl having 1 to 5 halogen atoms, or A represents the radical of the formula (A9)

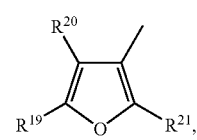

(A9)

in which
- $R^{19}$ and $R^{20}$ independently of one another represent hydrogen, halogen, amino, $C_1$-$C_4$-alkyl or $C_1$-$C_4$-haloalkyl having 1 to 5 halogen atoms,
- $R^{21}$ represents hydrogen, halogen, $C_1$-$C_4$-alkyl or $C_1$-$C_4$-haloalkyl having 1 to 5 halogen atoms, or A represents the radical of the formula (A10)

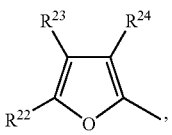

(A10)

in which
- $R^{22}$ and $R^{23}$ independently of one another represent hydrogen, halogen, amino, nitro, $C_1$-$C_4$-alkyl or $C_1$-$C_4$-haloalkyl having 1 to 5 halogen atoms,
- $R^{24}$ represents hydrogen, halogen, $C_1$-$C_4$-alkyl or $C_1$-$C_4$-haloalkyl having 1 to 5 halogen atoms, or A represents the radical of the formula (A11)

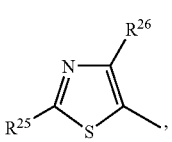

(A11)

in which
- $R^{25}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms,
- $R^{26}$ represents halogen, $C_1$-$C_4$-alkyl or $C_1$-$C_4$-haloalkyl having 1 to 5 halogen atoms, or A represents the radical of the formula (A12)

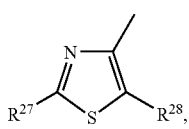

(A12)

in which
- $R^{27}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms,
- $R^{28}$ represents halogen, $C_1$-$C_4$-alkyl or $C_1$-$C_4$-haloalkyl having 1 to 5 halogen atoms, or A represents the radical of the formula (A13)

(A13)

in which
- $R^{29}$ represents halogen, $C_1$-$C_4$-alkyl or $C_1$-$C_4$-haloalkyl having 1 to 5 halogen atoms, or A represents the radical of the formula (A14)

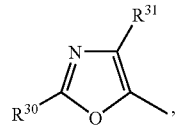
(A14)

in which
R$^{30}$ represents hydrogen or C$_1$-C$_4$-alkyl,
R$^{31}$ represents halogen or C$_1$-C$_4$-alkyl, or A represents the radical of the formula (A15)

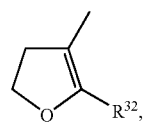
(A15)

in which
R$^{32}$ represents C$_1$-C$_4$-alkyl or C$_1$-C$_4$-haloalkyl having 1 to 5 halogen atoms, or A represents the radical of the formula (A16)

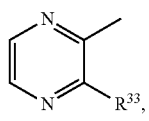
(A16)

in which
R$^{33}$ represents hydrogen, halogen, C$_1$-C$_4$-alkyl or C$_1$-C$_4$-haloalkyl having 1 to 5 halogen atoms, or A represents the radical of the formula (A17)

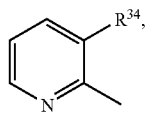
(A17)

in which
R$^{34}$ represents halogen, hydroxyl, C$_1$-C$_4$-alkyl, C$_1$-C$_4$-alkoxy, C$_1$-C$_4$-alkylthio, C$_1$-C$_4$-haloalkyl, C$_1$-C$_4$-haloalkylthio or C$_1$-C$_4$-haloalkoxy having in each case 1 to 5 halogen atoms, or A represents the radical of the formula (A18)

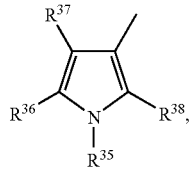
(A18)

in which
R$^{35}$ represents hydrogen, cyano, C$_1$-C$_4$-alkyl, C$_1$-C$_4$-haloalkyl having 1 to 5 halogen atoms, C$_1$-C$_4$-alkoxy-C$_1$-C$_4$-alkyl, hydroxy-C$_1$-C$_4$-alkyl, C$_1$-C$_4$-alkylsulphonyl, di(C$_1$-C$_4$-alkyl)aminosulphonyl, C$_1$-C$_6$-alkylcarbonyl or in each case optionally substituted phenylsulphonyl or benzoyl,
R$^{36}$ represents hydrogen, halogen, C$_1$-C$_4$-alkyl or C$_1$-C$_4$-haloalkyl having 1 to 5 halogen atoms,
R$^{37}$ represents hydrogen, halogen, cyano, C$_1$-C$_4$-alkyl or C$_1$-C$_4$-haloalkyl having 1 to 5 halogen atoms,
R$^{38}$ represents hydrogen, halogen, C$_1$-C$_4$-alkyl or C$_1$-C$_4$-haloalkyl having 1 to 5 halogen atoms, or A represents the radical of the formula (A19)

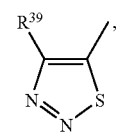
(A19)

in which
R$^{39}$ represents C$_1$-C$_4$-alkyl,
characterized in that
a) in a first step carbonyl halides of the formula (II)

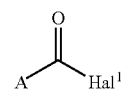
(II)

in which
A is as defined above and
Hal$^1$ represents fluorine, chlorine or bromine,
are reacted with acetophenone derivatives of the formula (III) or salts thereof

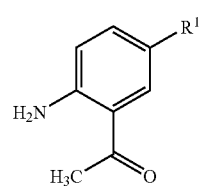
(III)

in which R$^1$ is as defined above,
if appropriate in the presence of an acid binder and if appropriate in the presence of a diluent, and b) the resulting acetylanilides of the formula (IV)

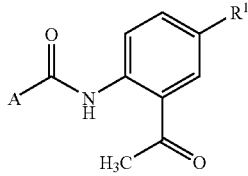
(IV)

in which A and R¹ are as defined above, are, in a second step, reacted with a Grignard reagent of the formula (V)

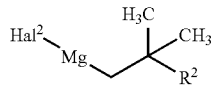
(V)

in which
R² is as defined above and
Hal² represents chlorine, bromine or iodine,
in the presence of a diluent,
and c) the resulting hydroxyalkylcarboxanilides of the formula (VI)

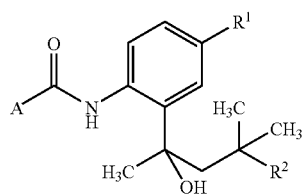
(VI)

in which R¹, R² and A are as defined above, are, in a last step analogously to the fourth step, hydrogenated in the presence of a catalyst and in the presence of a diluent, or initially, in an alternative third step, reacted in the presence of an acid and in the presence of a diluent,
and d) the resulting benzoxazines of the formula (VIIa) and alkenylanilides of the formulae (VIIb) and (VIIc)

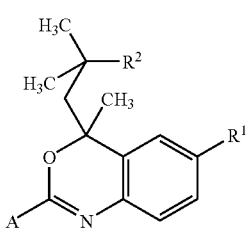
(VIIa)

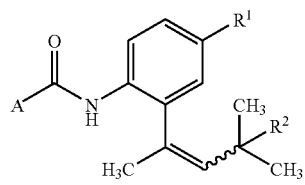
(VIIb)

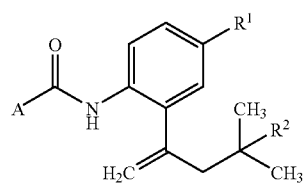
(VIIc)

in which R¹, R² and A are as defined above, are, in a fourth step, hydrogenated in the presence of a catalyst, if appropriate in the presence of an acid and in the presence of a diluent.

Surprisingly, the alkylanilides of the formula (I) can be prepared under the conditions according to the invention in good yields, with high purity and selectivity. The removal of the bases used by extractive processes, which is difficult owing to the poor solubility of (IV) can be avoided in an advantageous manner when, in a preferred variant of the process, the reaction of the first step is carried out without using a base, where the hydrogen halide liberated is, when the reaction is carried out in the heat, released into the gaseous phase.

In particular the right choice of solvent in the second step of the process according to the invention results in considerably enhanced yields compared to the processes of the prior art. In a preferred variant of step 2 of the process, solid, undissolved (IV) is added to an unpolar solvent, such as toluene, and the Grignard/ether solution is added simultaneously. In this manner, it can be avoided that the poorly soluble (IV) has to be dissolved in the required large amounts of a polar solvent unfavourable for the reaction, which would be necessary according to the prior art. Surprisingly, this is associated with a high increase in yield, since under classical conditions the reaction stops after little (IV) has been converted.

Once the third step has been carried out, unreacted (IV) can be recovered easily by stirring the product with heptane and selective precipitation of (IV).

Surprisingly, the third step (elimination of water) yields preferably the oxazine of the general formula (VIIa) in the case of short reaction times, whereas in the case of relatively long reaction times and using other water-limiting reagents, the preferred formation of the alkenylanilides (VIIb) and (VIIc) is observed. These in turn can be hydrogenated under milder conditions.

On the other hand, it is also possible to reduce hydroxyalkylcarboxanilides of the formula (VI) directly, without separate elimination of water.

Using, for example, 1,3-dimethyl-5-fluoro-4-pyrazolcarbonyl chloride and 2-aminoacetophenone as starting materials, the process according to the invention can be illustrated by the formula scheme below:

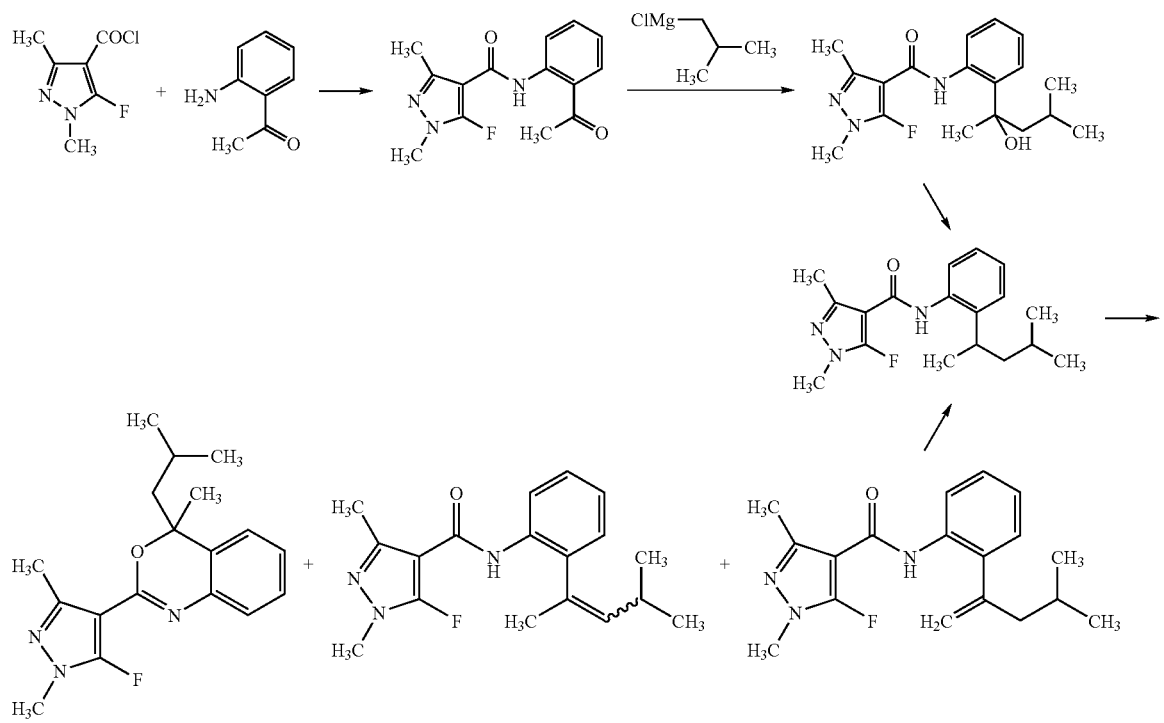

The formula (II) provides a general definition of the carbonyl halides used as starting materials for carrying out the process according to the invention. Hal¹ preferably represents fluorine or chlorine. The substituent A has the meanings A1 to A19 given above.

A preferably represents one of the radicals A1, A2, A3, A4, A5, A6, A9, A10, A11, A12, A16, A17 or A18.

A particularly preferably represents one of the radicals A1, A2, A3, A4, A5, A6, A9, A11, A16, A17, A18.

A very particularly preferably represents the radical A1.

A furthermore very particularly preferably represents the radical A2.

A furthermore very particularly preferably represents the radical A3.

A furthermore very particularly preferably represents the radical A4.

A furthermore very particularly preferably represents the radical A5.

A furthermore very particularly preferably represents the radical A6.

A furthermore very particularly preferably represents the radical A9.

A furthermore very particularly preferably represents the radical A11.

A furthermore very particularly preferably represents the radical A16.

A furthermore very particularly preferably represents the radical A17.

A furthermore very particularly preferably represents the radical A18.

In the radicals A1 to A19, the substituents given above have the preferred meanings below.

$R^3$ preferably represents hydrogen, cyano, fluorine, chlorine, bromine, iodine, methyl, ethyl, isopropyl, methoxy, ethoxy, methylthio, ethylthio, cyclopropyl, $C_1$-$C_2$-haloalkyl, $C_1$-$C_2$-haloalkoxy having in each case 1 to 5 fluorine, chlorine and/or bromine atoms, trifluoromethylthio, difluoromethylthio, aminocarbonyl, aminocarbonylmethyl or amino-carbonylethyl.

$R^3$ particularly preferably represents hydrogen, fluorine, chlorine, bromine, iodine, methyl, ethyl, isopropyl, monofluoromethyl, monofluoroethyl, difluoromethyl, trifluoromethyl, difluorochloromethyl, trichloromethyl, dichloromethyl, cyclopropyl methoxy, ethoxy, trifluoromethoxy, trichloromethoxy, methylthio, ethylthio, trifluoromethylthio or difluoromethylthio.

$R^3$ very particularly preferably represents hydrogen, fluorine, chlorine, bromine, iodine, methyl, isopropyl, monofluoromethyl, monofluoroethyl, difluoromethyl, trifluoromethyl, difluorochloromethyl or trichloromethyl.

$R^3$ especially preferably represents methyl, difluoromethyl, trifluoromethyl or 1-fluoroethyl.

$R^4$ preferably represents hydrogen, fluorine, chlorine, bromine, iodine, methyl, ethyl, methoxy, ethoxy, methylthio or ethylthio.

$R^4$ particularly preferably represents hydrogen, fluorine, chlorine, bromine, iodine or methyl.

$R^4$ very particularly preferably represents hydrogen, fluorine, chlorine or methyl.

$R^5$ preferably represents hydrogen, methyl, ethyl, n-propyl, isopropyl, $C_1$-$C_2$-haloalkyl having 1 to 5 fluorine, chlorine and/or bromine atoms, hydroxymethyl, hydroxyethyl, cyclopropyl, cyclopentyl, cyclohexyl or phenyl.

$R^5$ particularly preferably represents hydrogen, methyl, ethyl, isopropyl, trifluoromethyl, difluoromethyl, hydroxymethyl, hydroxyethyl or phenyl.

$R^5$ very particularly preferably represents hydrogen, methyl, trifluoromethyl or phenyl.

$R^5$ especially preferably represents methyl.

$R^6$ and $R^7$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^6$ and $R^7$ independently of one another particularly preferably represent hydrogen, fluorine, chlorine, bromine, methyl, ethyl, difluoromethyl, trifluoromethyl, difluorochloromethyl or trichloromethyl.

$R^6$ and $R^7$ independently of one another very particularly preferably represent hydrogen, fluorine, chlorine, bromine, methyl, ethyl, difluoromethyl, trifluoromethyl or trichloromethyl.

$R^6$ and $R^7$ especially preferably each represent hydrogen.

$R^8$ preferably represents fluorine, chlorine, bromine, cyano, methyl, ethyl, $C_1$-$C_2$-haloalkyl or $C_1$-$C_2$-haloalkoxy having in each case 1 to 5 fluorine, chlorine and/or bromine atoms.

$R^8$ particularly preferably represents fluorine, chlorine, bromine, cyano, methyl, trifluoromethyl, trifluoromethoxy, difluoromethoxy, difluorochloromethoxy or trichloromethoxy.

$R^8$ very particularly preferably represents fluorine, chlorine, bromine, iodine, methyl, trifluoromethyl or trifluoromethoxy.

$R^8$ especially preferably represents methyl.

$R^9$ and $R^{10}$ independently of one another preferably represent hydrogen, fluorine, chlorine, bromine, methyl, ethyl or $C_1$-$C_2$-haloalkyl having 1 to 5 fluorine, chlorine and/or bromine atoms.

$R^9$ and $R^{10}$ independently of one another particularly preferably represent hydrogen, fluorine, chlorine, bromine, methyl, ethyl, difluoromethyl, trifluoromethyl, difluorochloromethyl or tichloromethyl.

$R^9$ and $R^{10}$ independently of one another very particularly preferably represent hydrogen, fluorine, chlorine, bromine, methyl, ethyl, difluoromethyl, trifluoromethyl or trichloromethyl.

$R^9$ and $R^{10}$ especially preferably each represent hydrogen.

$R^{11}$ preferably represents hydrogen, fluorine, chlorine, bromine, methyl, ethyl or $C_1$-$C_2$-haloalkyl having 1 to 5 fluorine, chlorine and/or bromine atoms.

$R^{11}$ particularly preferably represents hydrogen, fluorine, chlorine, bromine, iodine, methyl or trifluoromethyl.

$R^{11}$ very particularly preferably represents methyl.

$R^{12}$ preferably represents hydrogen, fluorine, chlorine, bromine, iodine, hydroxyl, cyano, $C_1$-$C_4$-alkyl, $C_1$-$C_2$-haloalkyl, $C_1$-$C_2$-haloalkoxy or $C_1$-$C_2$-haloalkylthio having in each case 1 to 5 fluorine, chlorine and/or bromine atoms.

$R^{12}$ particularly preferably represents hydrogen, fluorine, chlorine, bromine, iodine, hydroxyl, cyano, methyl, ethyl, n-propyl, isopropyl, n-butyl, isobutyl, sec-butyl, tert-butyl, difluoromethyl, trifluoromethyl, difluorochloromethyl, trichloromethyl, trifluoromethoxy, difluoromethoxy, difluorochloromethoxy, trichloromethoxy, trifluoromethylthio, difluoromethylthio, difluorochloromethylthio or trichloromethylthio.

$R^{12}$ very particularly preferably represents hydrogen, fluorine, chlorine, bromine, iodine, methyl, difluoromethyl, trifluoromethyl or trichloromethyl.

$R^{12}$ especially preferably represents iodine, methyl, difluoromethyl or trifluoromethyl.

$R^{13}$ preferably represents fluorine, chlorine, bromine, iodine, hydroxyl, cyano, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{13}$ particularly preferably represents fluorine, chlorine, bromine, iodine, hydroxyl, cyano, methyl, ethyl, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, difluoromethylthio, trifluoromethylthio, trifluoromethoxy, difluoromethoxy, difluorochloromethoxy or trichloromethoxy.

$R^{13}$ very particularly preferably represents fluorine, chlorine, bromine, iodine, methyl, trifluoromethyl, difluoromethyl or trichloromethyl.

$R^{14}$ preferably represents hydrogen, fluorine, chlorine, bromine, iodine, cyano, $C_1$-$C_4$-alkyl, methoxy, ethoxy, methylthio, ethylthio, $C_1$-$C_2$-haloalkyl or $C_1$-$C_2$-haloalkoxy having in each case 1 to 5 fluorine, chlorine and/or bromine atoms, $C_1$-$C_2$-alkylsulphinyl or $C_1$-$C_2$-alkylsulphonyl.

$R^{14}$ particularly preferably represents hydrogen, fluorine, chlorine, bromine, iodine, cyano, n-propyl, isopropyl, n-butyl, isobutyl, sec-butyl, tert-butyl, trifluoromethyl, difluoromethyl, difluorochloromethyl, trichloromethyl, methoxy, ethoxy, methylthio, ethylthio, trifluoromethoxy, difluoromethoxy, difluorochloromethoxy, trichloromethoxy, methyl-sulphinyl or methylsulphonyl.

$R^{14}$ very particularly preferably represents hydrogen, fluorine, chlorine, bromine, iodine, n-propyl, isopropyl, n-butyl, isobutyl, sec-butyl, tert-butyl, trifluoromethyl, difluoromethyl, trichloromethyl, methylsulphinyl or methylsulphonyl.

$R^{14}$ especially preerably represents hydrogen.

$R^{15}$ preferably represents methyl, ethyl or $C_1$-$C_2$-haloalkyl having 1 to 5 fluorine, chlorine and/or bromine atoms.

$R^{15}$ particularly preferably represents methyl, ethyl, trifluoromethyl, difluoromethyl, difluorochloromethyl or trichloromethyl.

$R^{16}$ preferably represents methyl or ethyl.

$R^{16}$ particularly preferably represents methyl.

$Q^1$ preferably represents S (sulphur), $SO_2$ or $CH_2$.

$Q^1$ particularly preferably represents S (sulphur) or $CH_2$.

$Q^1$ very particularly preferably represents S (sulphur).

p preferably represents 0 or 1.

p particularly preferably represents 0.

$R^{17}$ preferably represents methyl, ethyl or $C_1$-$C_2$-haloalkyl having 1 to 5 fluorine, chlorine and/or bromine atoms.

$R^{17}$ particularly preferably represents methyl, ethyl, trifluoromethyl, difluoromethyl, difluorochloromethyl or trichloromethyl.

$R^{17}$ very particularly preferably represents methyl, trifluoromethyl, difluoromethyl or trichloromethyl.

$R^{18}$ preferably represents methyl, ethyl or $C_1$-$C_2$-haloalkyl having 1 to 5 fluorine, chlorine and/or bromine atoms.

$R^{18}$ particularly preferably represents methyl, ethyl, trifluoromethyl, difluoromethyl, difluorochloromethyl or trichloromethyl.

$R^{18}$ very particularly preferably represents methyl, trifluoromethyl difluoromethyl or trichloromethyl.

$R^{19}$ and $R^{20}$ independently of one another preferably represent hydrogen, fluorine, chlorine, bromine, amino, methyl, ethyl or $C_1$-$C_2$-haloalkyl having 1 to 5 fluorine, chlorine and/or bromine atoms.

$R^{19}$ and $R^{20}$ independently of one another preferably represent hydrogen, fluorine, chlorine, bromine, methyl, ethyl, trifluoromethyl, difluoromethyl, difluorochloromethyl or trichloromethyl.

$R^{19}$ and $R^{20}$ independently of one another very particularly preferably represent hydrogen, fluorine, chlorine, bromine, methyl, trifluoromethyl, difluoromethyl or trichloromethyl.

$R^{19}$ and $R^{20}$ especially preferably each represent hydrogen.

$R^{21}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{21}$ particularly preferably represents hydrogen, fluorine, chlorine, bromine, iodine, methyl, ethyl, trifluoromethyl, difluoromethyl, difluorochloromethyl or trichloromethyl.

$R^{21}$ very particularly preferably represents hydrogen, fluorine, chlorine, bromine, methyl, trifluoromethyl, difluoromethyl or trichloromethyl.

$R^{21}$ especially preferably represents methyl.

$R^{22}$ and $R^{23}$ independently of one another preferably represent hydrogen, fluorine, chlorine, bromine, amino, nitro, methyl, ethyl or $C_1$-$C_2$-haloalkyl having 1 to 5 fluorine, chlorine and/or bromine atoms.

$R^{22}$ and $R^{23}$ independently of one another particularly preferably represent hydrogen, fluorine, chlorine, bromine, nitro, methyl, ethyl, trifluoromethyl, difluoromethyl, difluorochloromethyl or trichloromethyl.

$R^{22}$ and $R^{23}$ independently of one another very particularly preferably represent hydrogen, fluorine, chlorine, bromine, methyl, trifluoromethyl, difluoromethyl or trichloromethyl.

$R^{22}$ and $R^{23}$ especially prfa each represent hydrogen.

$R^{24}$ preferably represents hydrogen, fluorine, chlorine, bromine, iodine, methyl, ethyl or $C_1$-$C_2$-haloalkyl having 1 to 5 fluorine, chlorine and/or bromine atoms.

$R^{24}$ particularly preferably represents hydrogen, fluorine, chlorine, bromine, iodine, methyl, ethyl, trifluoromethyl, difluoromethyl, difluorochloromethyl or trichloromethyl.

$R^{24}$ very particularly preferably represents hydrogen, fluorine, chlorine, bromine, methyl, trifluoromethyl, difluoromethyl or trichloromethyl.

$R^{24}$ especially preferably represents methyl.

$R^{25}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{25}$ particularly preferably represents hydrogen, fluorine, chlorine, bromine, amino, methyl-amino, dimethylamino, cyano, methyl, ethyl, trifluoromethyl, difluoromethyl, difluorochloromethyl or trichloromethyl.

$R^{25}$ very particularly preferably represents hydrogen, fluorine, chlorine, bromine, amino, methylamino, dimethylamino, methyl, trifluoromethyl, difluoromethyl or trichloromethyl.

$R^{25}$ especially preferably represents amino, methylamino, dimethylamino, methyl or trifluoromethyl.

$R^{26}$ preferably represents fluorine, chlorine, bromine, methyl, ethyl or $C_1$-$C_2$-haloalkyl having 1 to 5 fluorine, chlorine and/or bromine atoms.

$R^{26}$ particularly preferably represents fluorine, chlorine, bromine, methyl, ethyl, trifluoromethyl, difluoromethyl, difluorochloromethyl or trichloromethyl.

$R^{26}$ very particularly preferably represents fluorine, chlorine, bromine, methyl, trifluoromethyl, difluoromethyl or trichloromethyl.

$R^{26}$ especially preferably represents methyl, trifluoromethyl or difluoromethyl.

$R^{27}$ preferably represents hydrogen, fluorine, chlorine, bromine, amino, $C_1$-$C_4$-alkylamino, di($C_1$-$C_4$-alkyl)amino, cyano, methyl, ethyl or $C_1$-$C_2$-haloalkyl having 1 to 5 fluorine, chlorine and/or bromine atoms.

$R^{27}$ particularly preferably represents hydrogen, fluorine, chlorine, bromine, amino, methyl-amino, dimethylamino, cyano, methyl, ethyl, trifluoromethyl, difluoromethyl, difluorochloromethyl or trichloromethyl.

$R^{27}$ very particularly preferably represents hydrogen, fluorine, chlorine, bromine, amino, methylamino, dimethylamino, methyl, trifluoromethyl, difluoromethyl or trichloromethyl.

$R^{27}$ especially preferably represents amino, methylamino, dimethylamino, methyl or trifluoromethyl.

$R^{28}$ preferably represents fluorine, chlorine, bromine, methyl, ethyl or $C_1$-$C_2$-haloalkyl having 1 to 5 fluorine, chlorine and/or bromine atoms.

$R^{28}$ particularly preferably represents fluorine, chlorine, bromine, methyl, ethyl, trifluoromethyl, difluoromethyl, difluorochloromethyl or trichloromethyl.

$R^{28}$ very particularly preferably represents fluorine, chlorine, bromine, methyl, trifluoromethyl, difluoromethyl or trichloromethyl.

$R^{28}$ represents methyl, trifluoromethyl or difluoromethyl.

$R^{29}$ preferably represents fluorine, chlorine, bromine, methyl, ethyl or $C_1$-$C_2$-haloalkyl having 1 to 5 fluorine, chlorine and/or bromine atoms.

$R^{29}$ particularly preferably represents fluorine, chlorine, bromine, methyl, ethyl, trifluoromethyl, difluoromethyl, difluorochloromethyl or trichloromethyl.

$R^{29}$ very particularly preferably represents fluorine, chlorine, bromine, methyl, trifluoromethyl, difluoromethyl or trichloromethyl.

$R^{30}$ preferably represents hydrogen, methyl or ethyl.

$R^{30}$ particularly preferably represents methyl.

$R^{31}$ preferably represents fluorine, chlorine, bromine, methyl or ethyl.

$R^{31}$ particularly preferably represents fluorine, chlorine or methyl.

$R^{32}$ preferably represents methyl, ethyl or $C_1$-$C_2$-haloalkyl having 1 to 5 fluorine, chlorine and/or bromine atoms.

$R^{32}$ particularly preferably represents methyl, ethyl, trifluoromethyl, difluoromethyl, difluorochloromethyl or trichloromethyl.

$R^{32}$ very particularly preferably represents methyl, trifluoromethyl, difluoromethyl or trichloromethyl.

$R^{32}$ especially preferably represents methyl or trifluoromethyl.

$R^{33}$ preferably represents hydrogen, fluorine, chlorine, bromine, methyl, ethyl or $C_1$-$C_2$-haloalkyl having 1 to 5 fluorine, chlorine and/or bromine atoms.

$R^{33}$ particularly preferably represents hydrogen, fluorine, chlorine, bromine, methyl or trifluoromethyl.

$R^{34}$ preferably represents fluorine, chlorine, bromine, iodine, hydroxyl, $C_1$-$C_4$-alkyl, methoxy, ethoxy, methylthio, ethylthio, difluoromethylthio, trifluoromethylthio, $C_1$-$C_2$-haloalkyl or $C_1$-$C_2$-haloalkoxy having in each case 1 to 5 fluorine, chlorine and/or bromine atoms.

$R^{34}$ particularly preferably represents fluorine, chlorine, bromine, iodine, methyl, ethyl, n-propyl, isopropyl, n-butyl, isobutyl, sec-butyl, tert-butyl, trifluoromethyl, difluoromethyl, difluorochloromethyl or trichloromethyl.

$R^{34}$ very particularly preferably represents fluorine, chlorine, bromine, iodine, methyl, trifluoromethyl, difluoromethyl or trichloromethyl.

$R^{35}$ preferably represents hydrogen, methyl, ethyl, $C_1$-$C_2$-haloalkyl having 1 to 5 fluorine, chlorine and/or bromine atoms, $C_1$-$C_2$-alkoxy-$C_1$-$C_2$-alkyl, hydroxymethyl, hydroxyethyl, methylsulphonyl or dimethylaminosulphonyl.

$R^{35}$ particularly preferably represents hydrogen, methyl, ethyl, trifluoromethyl, methoxymethyl, ethoxymethyl, hydroxymethyl or hydroxyethyl.

$R^{35}$ very particularly preferably represents methyl or methoxymethyl.

$R^{36}$ preferably represents hydrogen, fluorine, chlorine, bromine, methyl, ethyl or $C_1$-$C_2$-haloalkyl having 1 to 5 fluorine, chlorine and/or bromine atoms.

$R^{36}$ particularly preferably represents hydrogen, fluorine, chlorine, bromine, methyl, ethyl, trifluoromethyl, difluoromethyl or trichloromethyl.

$R^{36}$ very particularly preferably represents hydrogen or methyl.

$R^{37}$ preferably represents hydrogen, fluorine, chlorine, bromine, iodine, cyano, methyl, ethyl, isopropyl or $C_1$-$C_2$-haloalkyl having 1 to 5 fluorine, chlorine and/or bromine atoms.

$R^{37}$ particularly preferably represents hydrogen, fluorine, chlorine, bromine, iodine, cyano, methyl, ethyl, isopropyl, trifluoromethyl, difluoromethyl, difluorochloromethyl or trichloromethyl.

$R^{37}$ very particularly preferably represents hydrogen, methyl, difluoromethyl or trifluoromethyl.

$R^{38}$ preferably represents hydrogen, fluorine, chlorine, bromine, methyl, ethyl or $C_1$-$C_2$-haloalkyl having 1 to 5 fluorine, chlorine and/or bromine atoms.

$R^{38}$ particularly preferably represents hydrogen, fluorine, chlorine, bromine, iodine, methyl or trifluoromethyl.

$R^{38}$ very particularly preferably represents hydrogen.

$R^{39}$ preferably represents methyl, ethyl, n-propyl or isopropyl.

$R^{39}$ particularly preferably represents methyl or ethyl.

The general or preferred radical definitions or illustrations given above can be combined between the respective ranges and preferred ranges as desired. They apply both to the end products and to the precursors and intermediates.

The carboxylic acid derivatives of the formula (II) are known and/or can be prepared by known processes (cf. WO 93/11117, EP-A 0 545 099, EP-A 0 589 301 and EP-A 0 589 313).

The formula (III) provides a general definition of the acetophenone derivatives furthermore used as starting materials for carrying out the process according to the invention. In this formula (III), $R^1$ preferably represents hydrogen. $R^1$ furthermore preferably represents fluorine.

Acetophenone derivatives of the formula (III) are known (cf. WO 03/010149).

The formula (IV) provides a general definition of the acetylanilides which occur as intermediates when carrying out the process according to the invention. In this formula (IV), A and $R^1$ have the preferred, particularly preferred, very particularly preferred and especially preferred meanings given above.

Some of the acetylanilides of the formula (IV) are known (cf. WO 03/010149). Acetylanilides of the formula (IV-a)

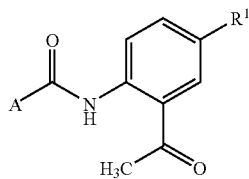

(IV-a)

in which A and $R^1$ are as defined above are novel, except for compounds in which A represents A1 and $R^4$ represents fluorine.

The formula (V) provides a general definition of the Grignard reagents furthermore used as starting materials for carrying out the process according to the invention. In this formula (V), $Hal^2$ preferably represents chlorine and $R^2$ has the preferred meanings below.

$R^2$ preferably represents hydrogen, fluorine, chlorine, bromine, iodine, methyl, ethyl, n- or isopropyl, n-, iso-, sec- or tert-butyl or represents methyl, ethyl, n- or isopropyl, n-, iso-, sec- or tert-butyl, each of which is mono- or polysubstituted by identical or different substituents from the group consisting of fluorine, chlorine and bromine.

$R^2$ particularly preferably represents hydrogen, fluorine, chlorine, bromine, methyl, ethyl, n- or isopropyl, n- or tert-butyl, trifluoromethyl, difluoromethyl, fluoromethyl, trichloromethyl, dichloromethyl, chloromethyl, chlorofluoromethyl, fluorodichloromethyl, difluorochloromethyl, pentafluoroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2-dichloro-2-fluoroethyl, 2,2,2-trichloroethyl, 1-chlorobutyl, heptafluoro-n-propyl or heptafluoroiso-propyl.

$R^2$ very particularly preferably represents hydrogen, chlorine, methyl, ethyl or trifluoromethyl.

The formula (VI) provides a general definition of the hydroxyalkylcarboxanilides which occur as intermediates when carrying out the process according to the invention. In this formula (VI), A, $R^1$ and $R^2$ have the preferred, particularly preferred, very particularly preferred and especially preferred meanings given above.

Some of the hydroxyalkylcarboxanilides of the formula (VI) are known and/or can be obtained by known processes (cf. WO 03/010149). Hydroxyalkylcarboxanilides of the formula (VI-a)

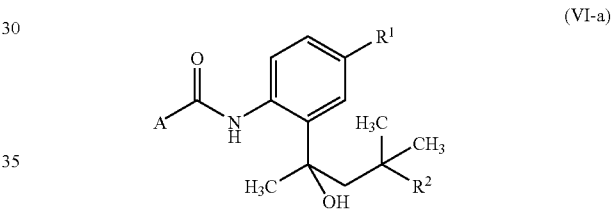

(VI-a)

in which A, $R^1$ and $R^2$ are as defined above are novel, except for compounds in which A represents A1 and $R^4$ represents fluorine.

The formula (VIIa) provides a general definition of the benzoxazines which furthermore occur as intermediates when carrying out the process according to the invention. In this formula (VIIa), A, $R^1$ and $R^2$ have the preferred, particularly preferred, very particularly preferred and especially preferred meanings given above.

Benzoxazines of the formula (VIIa) are novel. They also form part of this application and are obtained by steps one to three of the process according to the invention.

The formulae (VIIb) and (VIIc) provide a general definition of the alkenylanilides which furthermore occur as intermediates when carrying out the process according to the invention. In these formulae (VIIb) and (VIIc), A, $R^1$ and $R^2$ have the preferred, particularly preferred, very particularly preferred and especially preferred meanings given above.

Some of the alkenylanilides of the formulae (VIIb) and (VIIc) are known (cf. EP-A 0 824 099).

The first step of the process according to the invention can be carried out in the presence of an acid binder (a base) or else without acid binder (base), where the hydrochloric acid formed is given off on heating.

If a base is used, all customary inorganic or organic bases are suitable for carrying out the first step of the process according to the invention. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium tert-amyloxide, potassium tert-amyloxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N-ethyldiisopropylamine, N,N-dimethylaniline, N,N-dimethylbenzylamine, pyridine, picoline, ethylmethylpyridine, N-methylpiperidine, N-methylmorpholine, N,N-dimethylaminopyridine, diazabicyclooctane (DABCO), diazabicyclononene (DBN) or diazabicycloundecene (DBU). Particular preference is given to using potassium carbonate, sodium hydroxide, potassium hydroxide or pyridine.

Suitable diluents for carrying out the first step of the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofnn, 1,2-dimethoxyethane, 1,2-diethoxy-ethane or anisol; nitriles, such as acetonitrile, propionitrile, n- or i-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane; carboxylic acids, such as formic acid or acetic acid. Particularly preferably, the reaction is carried out in acetonitrile, N,N-dimethylformamide, N,N-dimethylacetamide, N-methylpyrrolidone, toluene or tetrahydrofuran.

When carrying out the first step of the process according to the invention, the reaction temperatures can be varied within a relatively wide range. In general, the process is carried out at temperatures of from −10° C. to +150° C.

When carrying out the first step of the process according to the invention, in general between 0.8 and 1.5 mol, preferably equimolar amounts, of the carbonyl halide of the formula (II) are employed per mole of the acetophenone derivative of the formula (III).

Depending on the reactivity of the starting materials, the reaction time may be up to 30 hours, but the reaction may be terminated earlier if complete conversion has been achieved.

The second step of the process according to the invention is carried out in aliphatic or aromatic hydrocarbons, such as petroleum ether, hexane, heptane, cyclohexane, methylcyclohexane, xylene, toluene, benzene or ethers, such as tetrahydrofuran, methyl tert-butyl ether, diethyl ether or in mixtures of the solvents mentioned, but preferably in toluene, if appropriate with addition of tetrahydrofuran, as diluent.

When carrying out the second step of the process according to the invention, the reaction temperatures may be varied within a relatively wide range. In general, the process is carried out at temperatures of from −30° C. to 50° C., preferably at temperatures of from −10° C. to 25° C.

When carrying out the second step of the process according to the invention, in general between 1.5 and 3 mol, preferably between 2 and 2.5 mol, of Grignard reagent of the formula (V) are employed per mole of the acetylanilide of the formula (IV). Part of the Grignard reagent may also be replaced by a base, such as, for example, a metal hydride; however, in this case at least 1 mol of Grignard reagent is required.

The second step of the process according to the invention is generally carried out using, as preferred solvent, toluene which is initially charged. The two starting materials [acetylanilide of the formula (IV) and Grignard reagent of the formula (V)] are then added to the solvent. In this manner, a conversion of more than 80% is achieved, whereas in the case of a customary practice of such a reaction (using tetrahydrofuran in which the starting material is dissolved, with subsequent addition of Grignard reagent) only 30% is achieved. By carrying out the reaction at relatively low temperatures, unwanted side reactions such as, for example, the exchange of halogens in the heterocyclic moiety for the Grignard alkyl group are reduced.

The elimination of water in the third step of the process according to the invention is carried out with acidic catalysis. Depending on the conditions, the benzoxazine and the isomeric pyrazolyl-alkenylanilides are obtained in varying compositions. However, the process according to the invention can also be implemented without carrying out the third step by subjecting the product of the second step directly to the conditions of the fourth step (hydrogenation).

Suitable diluents for carrying out the third step of the process according to the invention are all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 2-methyltetrahydrofuran, 1,2-dimethoxyethane, 1,2-diethoxyethane, 1,1-diethoxymethane, or anisol; alcohols, such as methanol, ethanol; nitriles, such as acetonitrile, propionitrile, n- or i-butyronitrile or benzonitrile; amides, such as N,N-dimethylformamide, N,N-dimethylacetamide, N-methylformanilide or N-methylpyrrolidone; esters, such as methyl acetate or ethyl acetate; sulphoxides, such as dimethyl sulphoxide; or sulphones, such as sulpholane; ketones, such as acetone or methyl isobutyl ketone; carboxylic acids, such as formic acid or acetic acid; or mixtures of these. Particularly preferably, the reaction is carried out in toluene, xylene, acetonitrile, ethyl acetate, tetrahydrofuran, dioxane, methanol, ethanol or mixtures thereof.

The addition of water scavengers, such as orthoesters, molecular sieve or removal of the water formed by azeotropic distillation is also advantageous.

Suitable acids for carrying out the third step of the process according to the invention are, for example, p-toluenesulphonic acid, trifluoroacetic acid, sulphuric acid, hydrochloric acid, hydrobromic acid, phosphoric acid, or acid chlorides (such as, for example, $POCl_3$, $SOCl_2$, $COCl_2$).

The reaction is preferably carried out at from 60 to 140° C. or at the boiling point of the solvent using reaction times of from 1 h to 48 h, shorter reaction times favouring the formation of the benzoxazine longer reaction times favouring the pyrazolylalkenylanilides. Orthoesters are added, for example, in equimolar amounts, whereas the acids may be added in catalytic amounts of 0.1-20% by weight, preferably 1-10% by weight.

The fourth step of the process according to the invention is carried out in the presence of a catalyst. Suitable catalysts are all catalysts customarily used for hydrogenations. Raney nickel, palladium, palladium hydroxide, rhodium or platinum, if appropriate on a support, such as, for example, activated carbon, may be mentioned by way of example.

Suitable diluents for carrying out the fourth step of the process according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisol, or alcohols, such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether; acids, also in catalytic amounts, such as acetic acid, hydrochloric acid, hydrobromic acid, sulphuric acid, perchloric acid, trifluoroacetic acid; esters, such as methyl acetate, isopropyl acetate, ethyl acetate.

The process according to the invention is generally carried out under slightly elevated pressure. However, depending on the catalyst used and the temperature, it is also possible to operate under elevated or reduced pressure—in general between 0.1 bar and 50 bar, preferably between 1 bar and 10 bar.

The reaction temperature is in a range between 0 and 150° C., preferably between 20 and 100° C.

The reaction time is not critical and can be selected from a relatively large range of from 1 h to 40 h, preferably from 6 h to 24 h, depending on the batch size.

The alkylanilides of the formula (I) preparable by the process according to the invention are useful fungicides (cf. WO 03/010149).

The preparation according to the invention of alkylanilides of the formula (I) is described in the examples below, which further illustrate the above description. However, the examples are not to be interpreted in a limiting manner.

PREPARATION EXAMPLES

Step 1: N-(2-Acetylphenyl)-5-fluoro-1,3-dimethyl-1H-pyrazole-4-carboxamide

From the Acid Chloride

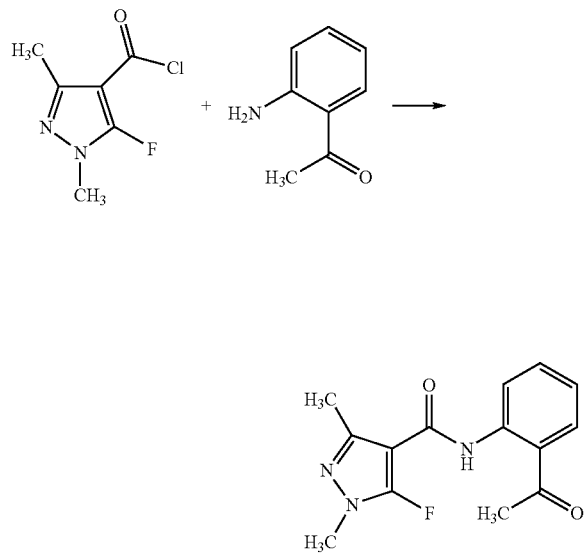

With stirring at 0° C., a solution of 1,3-dimethyl-5-fluoro-4-pyrazolecarbonyl chloride (58.79 g, 333.3 mmol) in 170 ml of toluene is added dropwise to a solution of 2-aminoacetophenone (45 g, 333.3 mmol) in toluene (570 ml). The solution becomes turbid and is allowed to warm to room temperature. It is then boiled at reflux for 7 h, with evolution of HCl gas with foaming. The mixture is allowed to cool and the precipitated crystals are filtered off with suction after 12 h. The crystals are then stirred vigorously in 300 ml of sodium bicarbonate solution, filtered off with suction and washed with water. After drying, 82.6 g (90% of theory) of the target compound N-(2-acetylphenyl)-5-fluoro-1,3-dimethyl-1H-pyrazole-4-carboxamide are obtained.

From the Acid Fluoride

A solution of 2-aminoacetophenone (405 mg, 3 mmol) and 1,3-dimethyl-5-fluoro-4-pyrazolecarbonyl fluoride (501 mg, 3 mmol) in toluene (7 ml) is boiled for 20 h, with addition of another 11% of the amount of pyrazole acid fluoride after 16 h. The hydrogen fluoride released is passed through dilute aqueous sodium hydroxide solution. The mixture is allowed to cool and the precipitated crystals are filtered off with suction after 12 h. They are then washed with toluene. After drying, 598 mg (65% of theory) of the target compound N-(2-acetylphenyl)-5-fluoro-1,3-dimethyl-1H-pyrazole-4-carboxamide are obtained in a purity of 89% (GC).

Step 2: 5-Fluoro-N-[2-(1-hydroxy-1,3-dimethybutyl) phenyl]-1,3-dimethyl-1-H-pyrazole-4-carboxamide

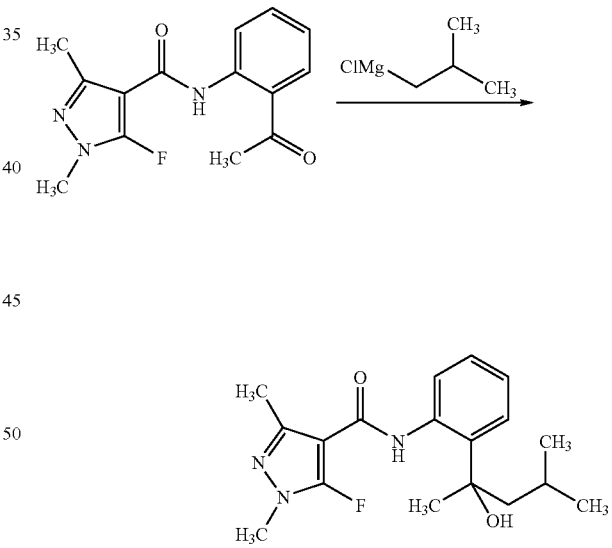

Under argon and with stirring at −10° C., N-(2-acetylphenyl)-5-fluoro-1,3-dimethyl-1H-pyrazole-4-carboxamide (as a solid, 10 g, 36.3 mmol) and isobutylmagnesium chloride (as a 2 M solution in THF, 41.7 ml; 83.55 mmol) are added simultaneously and continuously to 400 ml of toluene over a period of 150 minutes. The mixture is allowed to warm to room temperature, 200 ml of ammonium chloride solution are added, the mixture is extracted three times with in each case 100 ml of ethyl acetate and the organic phases are dried using sodium sulphate and concentrated under reduced pressure. This gives 5-fluoro-N-[2-(1-hydroxy-1,3-dimethylbutyl)

phenyl]-1,3-dimethyl-1H-pyrazole-4-carboxamide (14.2 g, purity (GC/MS) 72.8%; 85% of theory) which still contains 14% of starting material.

Step 3: 2-(5-Fluoro-1,3-dimethyl-1H-pyrazol-4-yl)-4-isobutyl-4-methyl-4H-3,1-benzoxazine

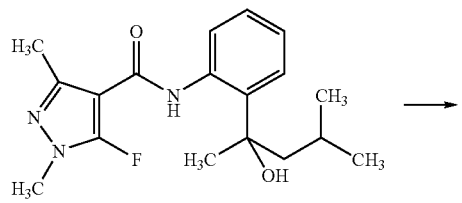

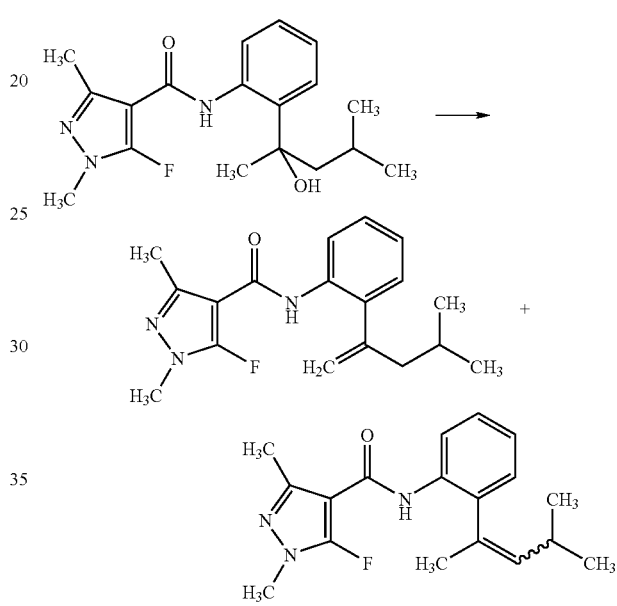

The above product from step 2 is boiled in 150 ml of toluene with 0.2 g of p-toluenesulphonic acid on a water separator for 2 h. The mixture is washed with aqueous sodium bicarbonate solution and the organic phase is concentrated under reduced pressure. By stirring with heptane, it is possible to precipitate and remove by filtration the N-(2-acetylphenyl)-5-fluoro-1,3-dimethyl-1H-pyrazole-4-carboxamide still present from the previous step. Chromatography gives 7.2 g (purity 85.1%; 63% of theory) of 2-(5-fluoro-1,3-dimethyl-1H-pyrazol-4-yl)-4-isobutyl-4-methyl-4H-3,1-benzoxazine.

Variant with Trimethyl Orthoformate

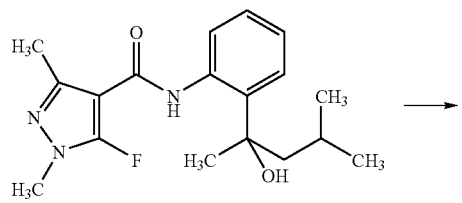

14 g (80% pure, 33.6 mmol) of 5-fluoro-N-[2-(1-hydroxy-1,3-dimethylbutyl)phenyl]-1,3-dimethyl-1H-pyrazole-4-carboxamide and 4.28 g (40.3 mmol) of trimethyl orthoformate are dissolved in 420 ml of toluene, and 5 drops of concentrated sulphuric acid are added. The solution is boiled for 1 h, treated with sodium sulphate and filtered off, and the filtrate is concentrated under reduced pressure. The residue is treated with 300 ml of heptane. This results in the N-(2-acetylphenyl)-5-fluoro-1,3-dimethyl-1H-pyrazole-4-carboxamide still present in the starting material precipitating out. The filtrate is concentrated using a rotary evaporator, giving 10.7 g of a yellow oil. Examination by GC/MS shows the following composition: 24% A, 25% B, 29% C and 7% of a methanol adduct.

Variant with Longer Reaction Time

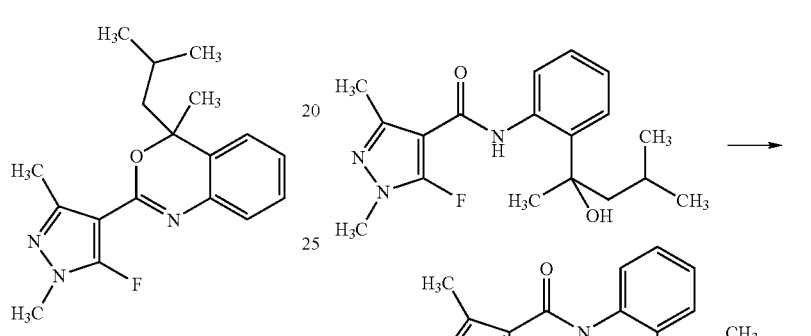

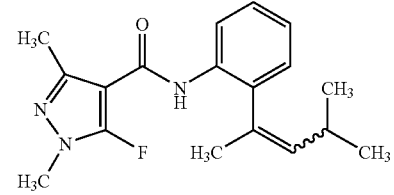

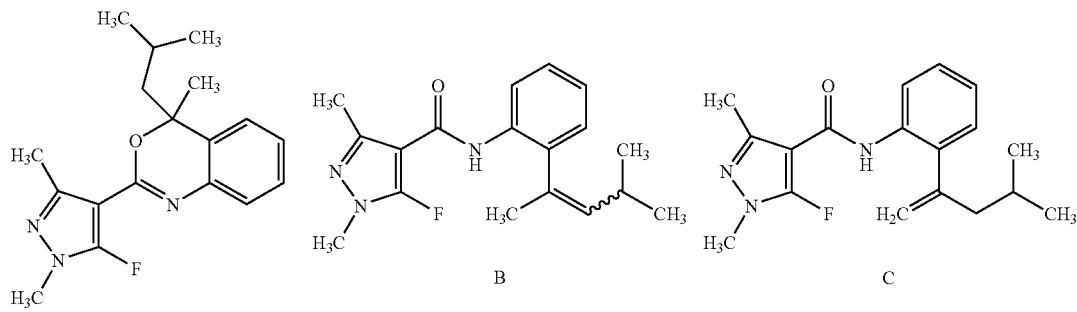

A  B  C

5-Fluoro-N-[2-(1-hydroxy-1,3-dimethylbutyl)phenyl]-1,3-dimethyl-1H-pyrazole-4-carboxamide (70 g, purity 99%, 208 mmol) is boiled in 1.4 l of toluene with p-toluenesulphonic acid (2 g) on a water separator for 40 hours. The mixture is washed with 50 ml of aqueous sodium bicarbonate solution and the organic phase is concentrated under reduced pressure. This gives 64.3 g of an oil which, according to GC/MS, consists of 18% 5-fluoro-1,3-dimethyl-N-[2-(3-methyl-1-methylenebutyl)phenyl]-1H-pyrazole-4-carboxamide and 18 and 58%, respectively, of N-{2-[(1Z and E)-1,3-dimethylbut-1-en-1-yl]phenyl}-5-fluoro-1,3-dimethyl-1H-pyrazole-4-carboxamide. N-{2-[1,3-Dimethylbut-1-en-1-yl]phenyl}-5-fluoro-1,3-dimethyl-1H-pyrazole-4-carboxamide:

$^1$H-NMR (400 MHz; CDCl$_3$): δ=1.05 (d, 6H, 2CH3), 1.95 (s, 31, CH3); 3.72 (s, 3H, CH3), 5.32 (d, 1H, C=C—H), 7.05 (m, 2H), 7.25 (m, 1H); 7.76 (s, 1H, NH), 8.31 (d, 1H)

Step 4: N-[2-(1,3-Dimethylbutyl)phenyl]-5-fluoro-1,3-dimethyl-1H-pyrazole-4-carboxamide

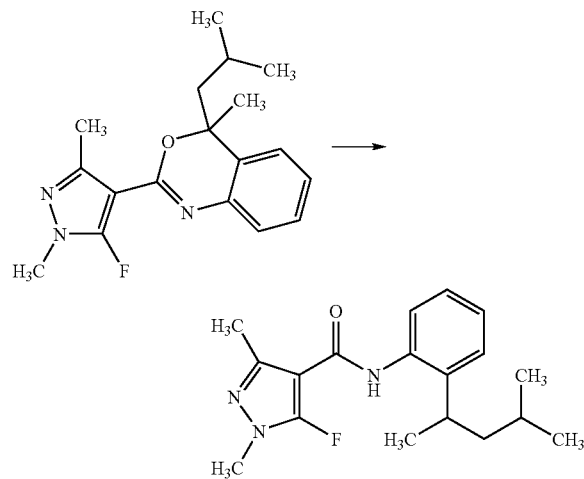

Hydrogenation of the Benzoxazine 1 g of 2-(5-fluoro-1,3-dimethyl-1H-pyrazol-4-yl)-4-isobutyl-4-methyl-4H-3,1-benzoxazine in 30 ml of glacial acetic acid is hydrogenated with 250 mg of Pd—C (50% in water) in an autoclave at room temperature under a hydrogen pressure of 2 bar for 5 h. The mixture is filtered off with suction through Celite, the filter cake is washed with ethyl acetate and the filtrate is concentrated under reduced pressure. The residue obtained in this manner is taken up in ethyl acetate, washed with water, dried and concentrated using a rotary evaporator. The residue is then taken up in heptane and again concentrated under reduced pressure, and the resulting clear oil is dried under reduced pressure. The oil begins to crystallize (1.05 g).

GC/MS: 82.6% of N-[2-(1,3-dimethylbutyl)phenyl]-5-fluoro-1,3-dimethyl-1H-pyrazole-4-carboxamide.

Hydrogenation of the Mixture of Benzoxazine and Pyrazolylalkenylanilides

At room temperature and under a hydrogen pressure of 20 bar, 10 g of the mixture of 24% A, 25% B, 29% C are prehydrogenated in 150 ml of glacial acetic acid using 350 mg of 10% Pd on carbon for 5 minutes. This mixture is added to a suspension of 1.38 g of Pd on carbon (10%) which was also prehydrogenated at 20 bar for 5 minutes. The combined mixture is then hydrogenated at room temperature and a hydrogen pressure of 5 bar for 5 hours. The mixture is filtered off with suction through Celite, the filter cake is washed with ethyl acetate and the filtrate is concentrated under reduced pressure. The residue obtained in this manner is taken up in ethyl acetate, washed with saturated sodium bicarbonate solution, dried and concentrated using a rotary evaporator. This gives a crystallizing oil (9.39 g).

GC/MS: 75.6% of N-[2-(1,3-dimethylbutyl)phenyl]-5-fluoro-1,3-dimethyl-1H-pyrazole-4-carboxamide.

Hydrogenation of N-{2-[(1Z and E)-1,3-dimethylbut-1-en-1-yl]phenyl}-5-fluoro-1,3-dimethyl-1H-pyrazole-4-carboxamide 1 g (82% pure, 2.6 mmol) of N-{2-[(1Z and E)-1,3-dimethylbut-1-en-1-yl]phenyl}-5-fluoro-1,3-dimethyl-1H-pyrazole-4-carboxamide is dissolved in 30 ml of methanol, and 100 mg of 10% palladium on carbon is added. The mixture is hydrogenated in an autoclave at a hydrogen pressure of 50 bar and at 40° C. for 19 hours. The catalyst is filtered off through Celite and the solution is concentrated under reduced pressure.

This gives 0.9 g of a crystallizing oil.

Content (GC-MS): 88.9% (97% of theory) of N-[2-(1,3-dimethylbutyl)phenyl]-5-fluoro-1,3-dimethyl-1H-pyrazole-4-carboxamide.

Hydrogenation of N-{2-[(1Z and E)-1,3-dimethylbut-1-en-1-yl]phenyl}-5-fluoro-1,3-dimethyl-1H-pyrazole-4-carboxamide 12 g (92.2% pure, 35 mmol) of N-{2-[(1Z and E)-1,3-dimethylbut-1-en-1-yl]phenyl}-5-fluoro-1,3-dimethyl-1H-pyrazole-4-carboxamide (isomer ratio 18:65; contains 8% of the exo-compound) are dissolved in 120 ml of methanol, with 600 mg of 10% palladium on carbon and 2.3 g (contains 15.2 mmol of acid) of a mixture of 5 ml of concentrated sulphuric acid and 5 ml of water are added and the mixture is hydrogenated at a hydrogen pressure of 5 bar and at 21° C. for 24 hours. The catalyst is filtered off with suction through Celite and the filter cake is washed with ethyl acetate. The filtrate is concentrated, the residue is taken up in ethyl acetate and washed with saturated sodium bicarbonate solution and the organic phase is separated off and concentrated. This gives 11.1 g of beige crystals.

Content (GC-MS): 93.9% (93.6% of theory) of N-[2-(1,3-dimethylbutyl)phenyl]-5-fluoro-1,3-dimethyl-1H-pyrazole-4-carboxamide.

Hydrogenation of 5-fluoro-N-[2-(1-hydroxy-1,3-dimethylbutyl)phenyl]-1,3-dimethyl-1H-pyrazole-4-carboxamide 0.6 g of mixture of 5 ml of concentrated sulphuric acid and 5 ml of water are added to 40 ml of tetrahydrofuran. 2 g (99% pure, 5.95 mmol) of 5-fluoro-N-[2-(1-hydroxy-1,3-dimethylbutyl)phenyl]-1,3-dimethyl-1H-pyrazole-4-carboxamide and 50 mg of palladium hydroxide on carbon (Pd content 20%) are added, and the mixture is hydrogenated at a hydrogen pressure of 5 bar and at 90° C. for a total of 16 hours. The catalyst is filtered off with suction through Celite and the filter cake is washed with ethyl acetate. The filtrate is concentrated, the residue is taken up in ethyl acetate and washed with saturated sodium bicarbonate solution and the organic phase is separated off and concentrated. This gives 1.8 g of white crystals.

Content (GCMS): 98.2% (93.6% of theory) of N-[2-(1,3-dimethylbutyl)phenyl]-5-fluoro-1,3-dimethyl-1H-pyrazole-4-carboxamide.

Hydrogenation of 5-fluoro-N-[2-(1-hydroxy-1,3-dimethylbutyl)phenyl]-1,3-dimethyl-1H-pyrazole-4-carboxamide 40 g (99.2% pure, 119 mmol) of 5-fluoro-N-[2-(1-hydroxy-1,3-dimethylbutyl)phenyl]-1,3-dimethyl-1H-pyrazole-4-carboxamide in 400 ml of 2-methyltetrahydrofuran are hydrogenated with 3.63 g of a 64 percent strength (w/w) sulphuric acid and 1 g of 10% Pd/C at a hydrogen pressure of 5 bar and at 80° C. for 16 hours.

The mixture is filtered off with suction through Celite, the filter cake is washed with 100 ml of 2-methyltetrahydrofuran, the filtrate is washed with 20 ml of saturated sodium bicarbonate solution and the organic phase is concentrated under reduced pressure. The residue is dissolved in 30 ml of toluene at 60° C., cooled to 0° C. with stirring, filtered off with suction and washed with 20 ml of ice-cold toluene. This gives 33.2 g (87% of theory) of beige N-[2-(1,3-dimethylbutyl)phenyl]-5-fluoro-1,3-dimethyl-1H-pyrazole-4-carboxamide crystals of melting point 111-113° C., purity 98.8% (GC against standard).

The invention claimed is:

1. A process for preparing alkylanilides of the formula (I)

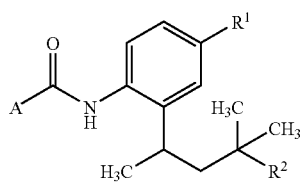

(I)

in which
R$^1$ represents hydrogen or fluorine,
R$^2$ represents hydrogen, halogen, C$_1$-C$_4$-alkyl or C$_1$-C$_4$-haloalkyl having 1 to 9 fluorine, chlorine or bromine atoms;
A represents the radical of the formula (A1)

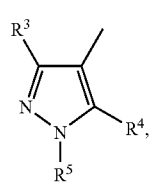

(A1)

in which
R$^3$ represents hydrogen, cyano, halogen, nitro, C$_1$-C$_4$-alkyl, C$_1$-C$_4$-alkoxy, C$_1$-C$_4$-alkylthio, C$_3$-C$_6$-cycloalkyl, C$_1$-C$_4$-haloalkyl, C$_1$-C$_4$-haloalkoxy or C$_1$-C$_4$-haloalkylthio having in each case 1 to 5 halogen atoms, aminocarbonyl or aminocarbonyl-C$_1$-C$_4$-alkyl,
R$^4$ represents hydrogen, halogen, cyano, C$_1$-C$_4$-alkyl, C$_1$-C$_4$-alkoxy or C$_1$-C$_4$-alkylthio, and
R$^5$ represents hydrogen, C$_1$-C$_4$-alkyl, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkoxy-C$_1$-C$_4$-alkyl, C$_1$-C$_4$-haloalkyl, C$_1$-C$_4$-haloalkylthio-C$_1$-C$_4$-alkyl, C$_1$-C$_4$-haloalkoxy-C$_1$-C$_4$-alkyl having in each case 1 to 5 halogen atoms, or phenyl,
or
A represents the radical of the formula (A2)

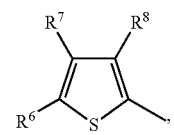

(A2)

in which
R$^6$ and R$^7$ independently of one another represent hydrogen, halogen, C$_1$-C$_4$-alkyl or C$_1$-C$_4$-haloalkyl having 1 to 5 halogen atoms, and
R$^8$ represents halogen, cyano, C$_1$-C$_4$-alkyl, or C$_1$-C$_4$-haloalkyl or C$_1$-C$_4$-haloalkoxy having in each case 1 to 5 halogen atoms,
or
A represents the radical of the formula (A3)

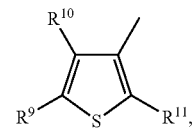

(A3)

in which
R$^9$ and R$^{10}$ independently of one another represent hydrogen, halogen, C$_1$-C$_4$-alkyl or C$_1$-C$_4$-haloalkyl having 1 to 5 halogen atoms, and
R$^{11}$ represents hydrogen, halogen, C$_1$-C$_4$-alkyl or C$_1$-C$_4$-haloalkyl having 1 to 5 halogen atoms,
or
A represents the radical of the formula (A4)

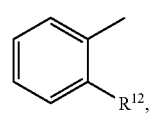

(A4)

in which
R$^{12}$ represents hydrogen, halogen, hydroxyl, cyano, C$_1$-C$_6$-alkyl, C$_1$-C$_4$-haloalkyl, C$_1$-C$_4$-haloalkoxy or C$_1$-C$_4$-haloalkylthio having in each case 1 to 5 halogen atoms,
or
A represents the radical of the formula (A5)

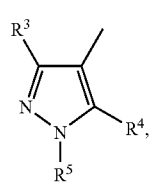

(A5)

in which
R$^{13}$ represents halogen, hydroxyl, cyano, C$_1$-C$_4$-alkyl, C$_1$-C$_4$-alkoxy, C$_1$-C$_4$-alkylthio, C$_1$-C$_4$-haloalkyl, $C_1$-$C_4$-haloalkylthio or $C_1$-$C_4$-haloalkoxy having in each case 1 to 5 halogen atoms, and $R^{14}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulfinyl or $C_1$-$C_4$-alkylsulfonyl, or A represents the radical of the formula (A6)

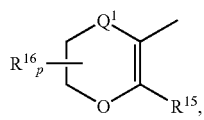
(A6)

in which
$R^{15}$ represents $C_1$-$C_4$-alkyl or $C_1$-$C_4$-haloalkyl having 1 to 5 halogen atoms,
$R^{16}$ represents $C_1$-$C_4$-alkyl,
$Q^1$ represents S (sulphur), O (oxygen), SO, $SO_2$ or $CH_2$, and
p represents 0, 1 or 2, where $R^{16}$ represents identical or different radicals if p represents 2, or A represents the radical of the formula (A7)

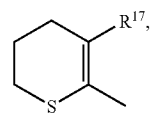
(A7)

in which
$R^{17}$ represents $C_1$-$C_4$-alkyl or $C_1$-$C_4$-haloalkyl having 1 to 5 halogen atoms, or A represents the radical of the formula (A8)

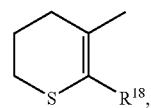
(A8)

in which
$R^{18}$ represents $C_1$-$C_4$-alkyl or $C_1$-$C_4$-haloalkyl having 1 to 5 halogen atoms, or A represents the radical of the formula (A9)

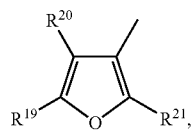
(A9)

in which
$R^{19}$ and $R^{20}$ independently of one another represent hydrogen, halogen, amino, $C_1$-$C_4$-alkyl or $C_1$-$C_4$-haloalkyl having 1 to 5 halogen atoms, and $R^{21}$ represents hydrogen, halogen, $C_1$-$C_4$-alkyl or $C_1$-$C_4$-haloalkyl having 1 to 5 halogen atoms, or A represents the radical of the formula (A10)

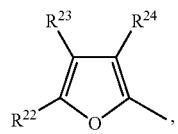
(A10)

in which
$R^{22}$ and $R^{23}$ independently of one another represent hydrogen, halogen, amino, nitro, $C_1$-$C_4$-alkyl or $C_1$-$C_4$-haloalkyl having 1 to 5 halogen atoms, and
$R^{24}$ represents hydrogen, halogen, $C_1$-$C_4$-alkyl or $C_1$-$C_4$-haloalkyl having 1 to 5 halogen atoms, or A represents the radical of the formula (A11)

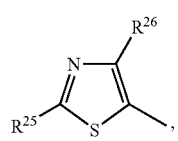
(A11)

in which
$R^{25}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms, and
$R^{26}$ represents halogen, $C_1$-$C_4$-alkyl or $C_1$-$C_4$-haloalkyl having 1 to 5 halogen atoms, or A represents the radical of the formula (A12)

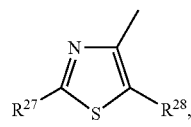
(A12)

in which
$R^{27}$ represents hydrogen, halogen, amino, $C_1$-$C_4$-alkylamino, di($C_1$-$C_4$-alkyl)amino, cyano, $C_1$-$C_4$-alkyl or $C_1$-$C_4$-haloalkyl having 1 to 5 halogen atoms, and
$R^{28}$ represents halogen, $C_1$-$C_4$-alkyl or $C_1$-$C_4$-haloalkyl having 1 to 5 halogen atoms, or A represents the radical of the formula (A13)

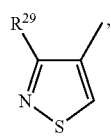
(A13)

in which
$R^{29}$ represents halogen, $C_1$-$C_4$-alkyl or $C_1$-$C_4$-haloalkyl having 1 to 5 halogen atoms, or A represents the radical of the formula (A14)

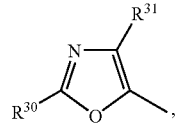
(A14)

in which
R$^{30}$ represents hydrogen or $C_1$-$C_4$-alkyl, and
R$^{31}$ represents halogen or $C_1$-$C_4$-alkyl,
or
A represents the radical of the formula (A15)

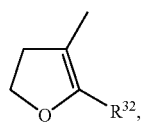
(A15)

in which
R$^{32}$ represents $C_1$-$C_4$-alkyl or $C_1$-$C_4$-haloalkyl having 1 to 5 halogen atoms,
or
A represents the radical of the formula (A16)

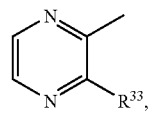
(A16)

in which
R$^{33}$ represents hydrogen, halogen, $C_1$-$C_4$-alkyl or $C_1$-$C_4$-haloalkyl having 1 to 5 halogen atoms,
or
A represents the radical of the formula (A17)

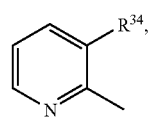
(A17)

in which
R$^{34}$ represents halogen, hydroxyl, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, or
A represents the radical of the formula (A18)

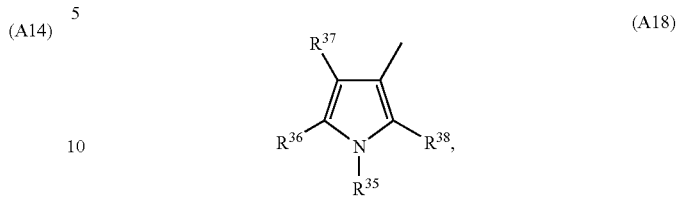
(A18)

in which
R$^{35}$ represents hydrogen, cyano, $C_1$-$C_4$-alkyl, $C_1$-$C_4$-haloalkyl having 1 to 5 halogen atoms, $C_1$-$C_4$-alkoxy-$C_1$-$C_4$-alkyl, hydroxy-$C_1$-$C_4$-alkyl, $C_1$-$C_4$-alkylsulfonyl, di($C_1$-$C_4$-alkyl)aminosulfonyl, $C_1$-$C_6$-alkylcarbonyl or in each case optionally substituted phenylsulfonyl or benzoyl,
R$^{36}$ represents hydrogen, halogen, $C_1$-$C_4$-alkyl or $C_1$-$C_4$-haloalkyl having 1 to 5 halogen atoms,
R$^{37}$ represents hydrogen, halogen, cyano, $C_1$-$C_4$-alkyl or $C_1$-$C_4$-haloalkyl having 1 to 5 halogen atoms, and
R$^{38}$ represents hydrogen, halogen, $C_1$-$C_4$-alkyl or $C_1$-$C_4$-haloalkyl having 1 to 5 halogen atoms,
or
A represents the radical of the formula (A19)

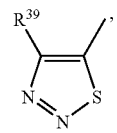
(A19)

in which
R$^{39}$ represents $C_1$-$C_4$-alkyl,
comprising:
a) reacting a carbonyl halide of the formula (II)

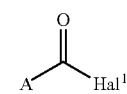
(II)

in which
A is a radical of formulae (A1), (A2), (A3), (A4), (A5), (A6), (A7), (A8), (A9), (A10), (A11), (A12), (A13), (A14), (A15), (A16), (A17), (A18), or (A19) defined above, and
Hal$^1$ represents fluorine, chlorine or bromine,
with an acetophenone derivative of the formula (III) or a salt thereof

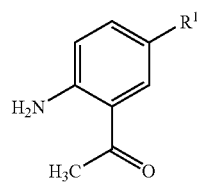
(III)

in which R¹ is hydrogen or fluorine,
optionally in the presence of an acid binder and optionally in the presence of a diluent,
to give
an acetylanilide of the formula (IV)

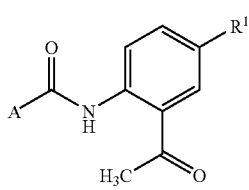
(IV)

in which A and R¹ are as defined above,
b) reacting a compound of formula (IV) with a Grignard reagent of the formula (V)

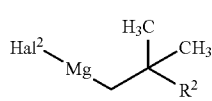
(V)

in which
R² is hydrogen, halogen, $C_1$-$C_4$-aklyl or $C_1$-$C_4$-haloalkyl having 1 to 9 fluorine, chlorine or bromine atoms, and
Hal² represents chlorine, bromine or iodine,
in the presence of a diluent,
to give
a hydroxyalkylcarboxanilide of the formula (VI)

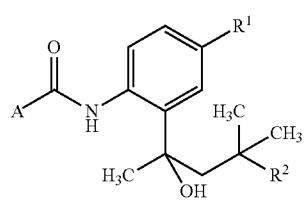
(VI)

in which R¹, R² and A are as defined above, and
c1) hydrogenating a compound of formula (VI) in the presence of a catalyst and in the presence of a diluent and an acid, to give a compound of formula (I);
or
c2) reacting a compound of formula (VI) in the presence of an acid and in the presence of a diluent,
to give a benzoxazine of the formula (VIIa) and an alkenylanilide of the formulae (VIIb) and (VIIc)

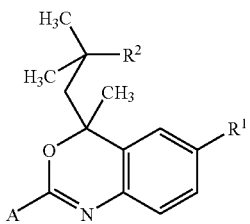
(VIIa)

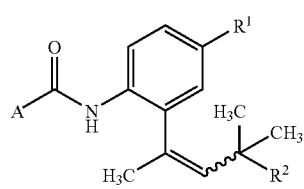
(VIIb)

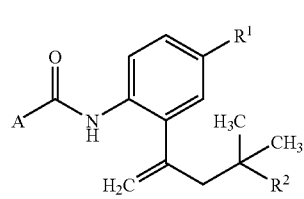
(VIIc)

in which R¹, R² and A are as defined above, and
d) hydrogenating a compound of formula (VIIa), (VIIb), or (VIIc) in the presence of a catalyst, optionally in the presence of an acid and in the presence of a diluent, to give a compound of formula (I).

2. The process of claim 1, wherein b) is carried out in toluene, toluene/tetrahydrofuran mixtures or toluene/methyl tert-butyl ether mixtures.

3. The process of claim 1, wherein in b) the solvent is initially charged and during the reaction a compound of formula (IV) and a compound of formula (V) are metered in simultaneously.

4. The process of claim 1, wherein said compound of formula (II) is 1,3-dimethyl-5-fluoro-4-pyrazolcarbonyl chloride or 1,3-dimethyl-5-fluoro-4-pyrazolcarbonyl fluoride, said compound of formula (III) is 2-aminoacetophenone and said compound of formula (V) is isobutylmagnesium chloride and the product obtained is N-[2-(1,3-dimethylbutyl)phenyl]-5-fluoro-1,3-dimethyl-1H-pyrazol-4-carboxamide.

5. A compound of formula (VIIa)

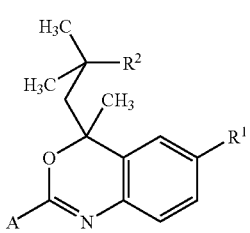
(VIIa)

in which
R¹ represents hydrogen or fluorine,
R² represents hydrogen, halogen, $C_1$-$C_4$-aklyl or $C_1$-$C_4$-haloalkyl having 1 to 9 fluorine, chlorine or bromine atoms;

A represents the radical of the formula (A1)

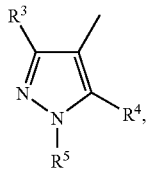
(A1)

in which
- $R^3$ represents hydrogen, cyano, halogen, nitro, $C_1$-$C_4$-alkyl, $C_1$-$C_4$-alkoxy, $C_1$-$C_4$-alkylthio, $C_3$-$C_6$-cycloalkyl, $C_1$-$C_4$-haloalkyl, $C_1$-$C_4$-haloalkoxy or $C_1$-$C_4$-haloalkylthio having in each case 1 to 5 halogen atoms, aminocarbonyl or aminocarbonyl-$C_1$-$C_4$-alkyl,
- $R^4$ represents hydrogen, halogen, cyano, $C_1$-$C_4$-alkyl, $C_1$-$C_4$-alkoxy or $C_1$-$C_4$-alkylthio, and
- $R^5$ represents hydrogen, $C_1$-$C_4$-alkyl, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl, $C_1$-$C_4$-haloalkyl, $C_1$-$C_4$-haloalkylthio-$C_1$-$C_4$-alkyl, $C_1$-$C_4$-haloalkoxy-$C_1$-$C_4$-alkyl having in each case 1 to 5 halogen atoms, or phenyl, or
A represents the radical of the formula (A2)

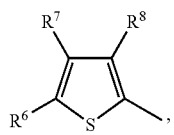
(A2)

in which
- $R^6$ and $R^7$ independently of one another represent hydrogen, halogen, $C_1$-$C_4$-alkyl or $C_1$-$C_4$-haloalkyl having 1 to 5 halogen atoms, and
- $R^8$ represents halogen, cyano, $C_1$-$C_4$-alkyl, or $C_1$-$C_4$-haloalkyl or $C_1$-$C_4$-haloalkoxy having in each case 1 to 5 halogen atoms, or
A represents the radical of the formula (A3)

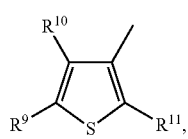
(A3)

in which
- $R^9$ and $R^{10}$ independently of one another represent hydrogen, halogen, $C_1$-$C_4$-alkyl or $C_1$-$C_4$-haloalkyl having 1 to 5 halogen atoms, and
- $R^{11}$ represents hydrogen, halogen, $C_1$-$C_4$-alkyl or $C_1$-$C_4$-haloalkyl having 1 to 5 halogen atoms, or
A represents the radical of the formula (A4)

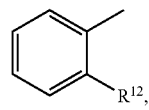
(A4)

in which
- $R^{12}$ represents hydrogen, halogen, hydroxyl, cyano, $C_1$-$C_6$-alkyl, $C_1$-$C_4$-haloalkyl, $C_1$-$C_4$-haloalkoxy or $C_1$-$C_4$-haloalkylthio having in each case 1 to 5 halogen atoms, or
A represents the radical of the formula (A5)

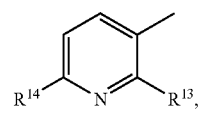
(A5)

in which
- $R^{13}$ represents halogen, hydroxyl, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkylthio or $C_1$-$C_4$-haloalkoxy having in each case 1 to 5 halogen atoms, and
- $R^{14}$ represents hydrogen, halogen, cyano, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy having in each case 1 to 5 halogen atoms, $C_1$-$C_4$-alkylsulfinyl or $C_1$-$C_4$-alkylsulfonyl, or
A represents the radical of the formula (A6)

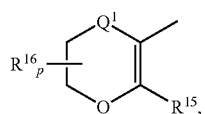
(A6)

in which
- $R^{15}$ represents $C_1$-$C_4$-alkyl or $C_1$-$C_4$-haloalkyl having 1 to 5 halogen atoms,
- $R^{16}$ represents $C_1$-$C_4$-alkyl,
- $Q^1$ represents S (sulphur), O (oxygen), SO, $SO_2$ or $CH_2$, and
- p represents 0, 1 or 2, where $R^{16}$ represents identical or different radicals if p represents 2, or
A represents the radical of the formula (A7)

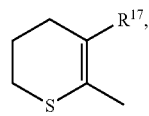
(A7)

in which
- $R^{17}$ represents $C_1$-$C_4$-alkyl or $C_1$-$C_4$-haloalkyl having 1 to 5 halogen atoms, or A represents the radical of the formula (A8)

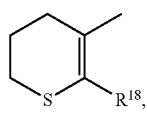
(A8)

in which
R$^{18}$ represents C$_1$-C$_4$-alkyl or C$_1$-C$_4$-haloalkyl having 1 to 5 halogen atoms, or A represents the radical of the formula (A9)

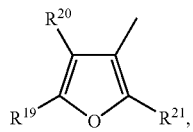
(A9)

in which
R$^{19}$ and R$^{20}$ independently of one another represent hydrogen, halogen, amino, C$_1$-C$_4$-alkyl or C$_1$-C$_1$-haloalkyl having 1 to 5 halogen atoms, and R$^{21}$ represents hydrogen, halogen, C$_1$-C$_4$-alkyl or C$_1$-C$_4$-haloalkyl having 1 to 5 halogen atoms, or A represents the radical of the formula (A10)

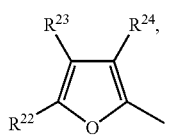
(A10)

in which
R$^{22}$ and R$^{23}$ independently of one another represent hydrogen, halogen, amino, nitro, C$_1$-C$_4$-alkyl or C$_1$-C$_4$-haloalkyl having 1 to 5 halogen atoms, and R$^{24}$ represents hydrogen, halogen, C$_1$-C$_4$-alkyl or C$_1$-C$_4$-haloalkyl having 1 to 5 halogen atoms, or A represents the radical of the formula (A11)

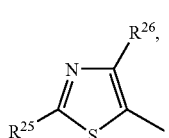
(A11)

in which
R$^{25}$ represents hydrogen, halogen, amino, C$_1$-C$_4$-alkylamino, di(C$_1$-C$_4$-alkyl)amino, cyano, C$_1$-C$_4$-alkyl or C$_1$-C$_4$-haloalkyl having 1 to 5 halogen atoms, and R$^{26}$ represents halogen, C$_1$-C$_4$-alkyl or C$_1$-C$_4$-haloalkyl having 1 to 5 halogen atoms, or A represents the radical of the formula (A12)

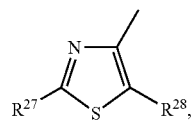
(A12)

in which
R$^{27}$ represents hydrogen, halogen, amino, C$_1$-C$_4$-alkylamino, di(C$_1$-C$_4$-alkyl)amino, cyano, C$_1$-C$_4$-alkyl or C$_1$-C$_4$-haloalkyl having 1 to 5 halogen atoms, and R$^{28}$ represents halogen, C$_1$-C$_4$-alkyl or C$_1$-C$_4$-haloalkyl having 1 to 5 halogen atoms, or A represents the radical of the formula (A13)

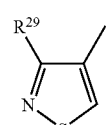
(A13)

in which
R$^{29}$ represents halogen, C$_1$-C$_4$-alkyl or C$_1$-C$_4$-haloalkyl having 1 to 5 halogen atoms, or A represents the radical of the formula (A14)

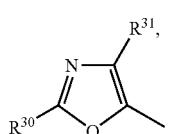
(A14)

in which
R$^{30}$ represents hydrogen or C$_1$-C$_4$-alkyl, and

R$^{31}$ represents halogen or C$_1$-C$_4$-alkyl, or

A represents the radical of the formula (A15)

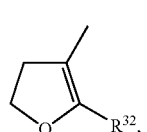
(A15)

in which
R$^{32}$ represents C$_1$-C$_4$-alkyl or C$_1$-C$_4$-haloalkyl having 1 to 5 halogen atoms, or
A represents the radical of the formula (A16)

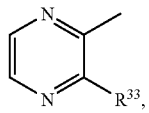
(A16)

in which
R$^{33}$ represents hydrogen, halogen, C$_1$-C$_4$-alkyl or C$_1$-C$_4$-haloalkyl having 1 to 5 halogen atoms,
or
A represents the radical of the formula (A17)

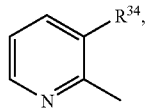
(A17)

in which
R$^{34}$ represents halogen, hydroxyl, C$_1$-C$_4$-alkyl, C$_1$-C$_4$-alkoxy, C$_1$-C$_4$-alkylthio, C$_1$-C$_4$-haloalkyl, C$_1$-C$_4$-haloalkylthio or C$_1$-C$_4$-haloalkoxy having in each case 1 to 5 halogen atoms,
or
A represents the radical of the formula (A18)

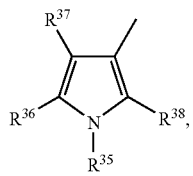
(A18)

in which
R$^{35}$ represents hydrogen, cyano, C$_1$-C$_4$-alkyl, C$_1$-C$_4$-haloalkyl having 1 to 5 halogen atoms, C$_1$-C$_4$-alkoxy-C$_1$-C$_4$-alkyl, hydroxy-C$_1$-C$_4$-alkyl, C$_1$-C$_4$-alkylsulfonyl, di(C$_1$-C$_4$-alkyl)aminosulfonyl, C$_1$-C$_6$-alkylcarbonyl or in each case optionally substituted phenylsulfonyl or benzoyl,
R$^{36}$ represents hydrogen, halogen, C$_1$-C$_4$-alkyl or C$_1$-C$_4$-haloalkyl having 1 to 5 halogen atoms,
R$^{37}$ represents hydrogen, halogen, cyano, C$_1$-C$_4$-alkyl or C$_1$-C$_4$-haloalkyl having 1 to 5 halogen atoms, and
R$^{38}$ represents hydrogen, halogen, C$_1$-C$_4$-alkyl or C$_1$-C$_4$-haloalkyl having 1 to 5 halogen atoms,
or
A represents the radical of the formula (A19)

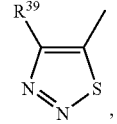
(A19)

in which
R$^{39}$ represents C$_1$-C$_4$-alkyl.

6. The process of claim 2, wherein in b) the solvent is initially charged and during the reaction a compound of formula (IV), preferably in solid form, and a compound of formula (V) are metered in simultaneously.

7. The process of claim 2, wherein said compound of formula (II) is 1,3-dimethyl-5-fluoro-4-pyrazolcarbonyl chloride or 1,3-dimethyl-5-fluoro-4-pyrazolcarbonyl fluoride, said compound of formula (III) is 2-aminoacetophenone, and said compound of formula (V) is isobutylmagnesium chloride, and the product obtained is N-[2-(1,3-dimethylbutyl)phenyl]-5-fluoro-1,3-dimethyl-1H-pyrazol-4-carboxamide.

8. The process of claim 3, wherein said compound of formula (II) is 1,3-dimethyl-5-fluoro-4-pyrazolcarbonyl chloride or 1,3-dimethyl-5-fluoro-4-pyrazolcarbonyl fluoride, said compound of formula (III) is 2-aminoacetophenone, and said compound of formula (V) is isobutylmagnesium chloride, and the product obtained is N-[2-(1,3-dimethylbutyl)phenyl]-5-fluoro-1,3-dimethyl-1H-pyrazol-4-carboxamide.

9. The process of claim 6, wherein said compound of formula (II) is 1,3-dimethyl-5-fluoro-4-pyrazolcarbonyl chloride or 1,3-dimethyl-5-fluoro-4-pyrazolcarbonyl fluoride, said compound of formula (III) is 2-aminoacetophenone, and said compound of formula (V) is isobutylmagnesium chloride, and the product obtained is N-[2-(1,3-dimethylbutyl)phenyl]-5-fluoro-1,3-dimethyl-1H-pyrazol-4-carboxamide.

10. The process of claim 3, wherein said compound of formula (IV) is in solid form.

* * * * *